United States Patent [19]

Tabata et al.

[11] Patent Number: 4,655,925
[45] Date of Patent: Apr. 7, 1987

[54] ACTIVATED SLUDGE METHOD

[75] Inventors: Shin-ichi Tabata, Funabashi; Tomio Suzuki, Tokyo; Youichi Hamamoto, Tokyo; Noboru Hayakawa, Tokyo; Kaoru Watanabe, Tokyo, all of Japan

[73] Assignee: Nishihara Environmental Sanitation Research Corporation Limited, Tokyo, Japan

[21] Appl. No.: 692,839

[22] Filed: Jan. 18, 1985

[30] Foreign Application Priority Data

Jan. 20, 1984 [JP] Japan .................................. 59-7250
Feb. 10, 1984 [JP] Japan ................................. 59-21814

[51] Int. Cl.$^4$ .............................................. C02F 3/30
[52] U.S. Cl. .................................. 210/605; 210/628; 210/903; 210/906
[58] Field of Search ............... 210/605, 614, 623, 626, 210/628-630, 903, 906

[56]  References Cited

U.S. PATENT DOCUMENTS 4,271,026  6/1981  Chen et al. ........................... 210/605
4,488,967  12/1984 Block et al. ......................... 210/605
4,522,722  6/1985  Nicholas ............................. 210/605

OTHER PUBLICATIONS

Barnard "A Review of Biological Phosphorus Removal in the Activated Sludge Process" (Water SA, vol. 2, No. 3, Jul. 1975).
Barnard, "Biological Nutrient Removal Without the Addition of Chemicals" (Water Research, vol. 9, 1975).
Bishop et al., "Single-Stage Nitrification-Denitrification" (Journal WPCF, vol. 48, No. 3, Mar. 1976).

Primary Examiner—Tom Wyse
Attorney, Agent, or Firm—Michael N. Meller

[57] ABSTRACT

A method of removing nitrogen and phosphorus from waste water by using an activated sludge including aerobic bacteria is disclosed. The waste water is fed continuously and gradually into a treatment basin in which the sludge is contained so that a mixed liquor consisting of the waste water and the sludge is formed therein. A cycle consisting of an agitating step and an aerating step is repeated at least two times and each cycle is finished within two hours, with the ratio of the agitating time to the aerating time being between one to one and to one. In the agitating step, the mixed liquor presents an anoxic condition and a succeeding anaerobic condition. Denitrification occurs in the anoxic condition and the aerobic bacteria release phosphorus in the anaerobic condition. During the aerating step, nitrification is caused while the bacteria excessively ingest phosphorus from the mixed liquor.

8 Claims, 9 Drawing Figures

ACTIVATED SLUDGE METHOD

BACKGROUND OF THE INVENTION

1. Field of the Invention

The present invention relates to an activated sludge method, and more particularly to a method of removing nitrogen and phosphorus from waste water by using activated sludge including aerobic bacteria.

2. Description of the Invention

Various activated sludge processes for removing nitrogen and/or phosphorus from waste water by using an activated sludge including aerobic bacteria have been proposed for the purpose of protecting enclosed water areas such as lakes and bays from eutrophication.

One of the activated sludge processes for denitrification and phosphorus removal is illustrated in FIGS. 1 and 2. FIG. 1 shows a tank 10 which has a baffle plate 12 provided therein. The baffle plate 12 divides the tank 10 into a basin 14 for pre-treating the waste water by a small amount of the sludge contained therein and a basin 16 for treating the waste water by the sludge contained in the tank 10, with a mixed liquor consisting of the waste water and the sludge being formed in the basin 16. An air diffuser 18 is disposed at the bottom of the treatment basin 16 to aerate the mixed liquor held in the treatment basin 16. FIG. 2 shows a time schedule along which the mixed liquor is treated. As shown in FIG. 2, the mixed liquor is aerated in the treatment basin 16 by the air diffuser 18 over a period of three hours. In this aerobic condition, nitrification is accomplished in the mixed liquor. That is, ammonia nitrogen included in the mixed liquor is nitrified and changed into nitrate nitrogen. On the other hand, phosphorus included in the mixed liquor is ingested by the sludge bacteria, with organic material included in the mixed liquor also being consumed. Then, the mixed liquor is allowed to settle over a period of one hour so that it is separated into a supernatant liquid and the sludge. After the settling is started, the mixed liquor presents an anoxic condition so that due to the existence of the sludge bacteria, nitrate nitrogen is subjected to reduction while the organic material is subjected to oxidization, thereby causing the denitrification. After settling is finished, the supernatant liquid is discharged as an effluent from the treatment basin 16 over a period of two hours while a new waste water is introduced into the treatment basin 16 through the pre-treatment basin 14. When the supernatant liquid is discharged, a decanter 20 as shown in FIG. 1, which is well known in this field, is used. On the other hand, the settled sludge is partially drawn out from the treatment basin 16, if necessary and the remainder is reused for treating the new waste water. As is apparent from FIG. 2, a cycle consisting of the aerating, settling and discharging stages takes six hours and is repeated four times per day.

The activated sludge process as discussed above is unsatisfactory because the denitrification and the phosphorus removal are achieved only at a low percentage (about 60%).

JAPANESE PATENT PUBLICATION No. 56 (1981)-53435 discloses an activated sludge process wherein a cycle consisting of agitating and aerating stages is repeated in a single tank in which a mixed liquor consisting of waste water and activated sludge is contained, and the agitating time and the aerating time are controlled in such a manner that the ratio of nitrate nitrogen to ammonia nitrogen is maintained within a predetermined range, whereby the denitrification is achieved with high efficiency. However, this activated sludge method is also unsatisfactory because almost no phosphorus removal is obtained, although the denitrification is highly efficiently achieved.

In general, for highly efficient removal of phosphorus from waste water by use of the activated sludge, it is necessary to put the mixed liquor under the anaerobic condition so that the aerobic bacteria releases phosphorus into the mixed liquor in order to stay alive. This is because the aerobic bacteria which have been stressed to release phosphorus then excessively ingest phosphorus from the mixed liquor so that phosphorus is removed from the waste water with high efficiency.

"Water SA", Vol. 2, No. 3, July, 1976 discloses an activated sludge process for conducting denitrification and phosphorus removal at a relatively high efficiency. This activated sludge process can be explained by a flow chart as shown in FIG. 3. In FIG. 3, first, the waste water is fed into an anaerobic basin 22 in which the sludge is contained so that a mixed liquor consisting of the waste water and sludge, is formed. The mixed liquor is kept in the basin 22 until phosphorus is released from the sludge bacteria. The mixed liquor is then transferred to an anoxic basin 24 where denitrification is carried out. The mixed liquor is further transferred to an aerobic basin 26 where phosphorus is excessively ingested by the sludge bacteria while the remaining ammonia nitrogen is nitrified and changed into nitrate nitrogen. In order for the denitrification, a part of the aerated mixed liquor is returned from the aerobic basin 26 to the anoxic basin 24. Thereafter, the mixed liquor is transferred from the aerobic basin 26 to a settling basin 28 where it is separated into a supernatant liquid and the sludge. The supernatant liquid is discharged as an effluent while the settled sludge is recycled to the anaerobic basin 22.

This activated sludge process is satisfactory in that the denitrification and the phosphorus removal can be achieved with a relatively high efficiency, but it entails the drawback of requiring the four basins 22, 24, 26 and 28 each of which must be of large capacity because the quantity of the mixed liquor to be held in each basin changes. In short, this process requires a large and expensive plant.

SUMMARY OF THE INVENTION

Accordingly, it is a principal object of the invention to provide a method of removing nitrogen and phosphorus at a high efficiency from waste water by using activated sludge including aerobic bacteria, wherein the drawbacks mentioned above can be eliminated.

It is a further object of the invention to provide a method as mentioned above wherein aeration is controlled so as to adjust the concentration of dissolved oxygen in a mixed liquor consisting of the waste water and the sludge to a predetermined value for ensuring highly efficient denitrification and phosphorus removal.

In order to achieve the principal object of the invention, the activated sludge method comprises the steps of: feeding the waste water continuously and gradually into a treatment basin in which the sludge is contained so that the mixed liquor consisting of the waste water and the sludge is formed; agitating the mixed liquor in said treatment basin until it presents an anoxic condition and a succeeding anaerobic condition so that denitrification is accomplished in the anoxic condition and phosphorus is then released from the sludge in the anaerobic condition; aerating the mixed liquor so that nitrification is caused while phosphorus is ingested by the sludge bacteria; repeating a cycle consisting of said agitating and aerating steps at least two times so that each cycle is finished within two hours, the ratio of the agitating time to the aerating time being between one to one and five to one; settling the agitated and aerated mixed liquor for separating it into a supernatant liquid and the sludge; and discharging the supernatant liquid as an effluent and reusing the settled sludge for the treatment of waste water.

In this method, the settling step may be carried out in the treatment basin. In this case, the feeding of the waste water into the treatment basin may be stopped or continued. When the waste water is continuously fed into the treatment basin during the settling step, it is subjected to a pretreatment by the settling sludge so that the succeeding treatment of the waste water is more effectively performed. On the other hand, the agitated and aerated mixed liquor may be transferred to a settling basin where the settling step is performed. In this case, the waste water is continuously treated.

In order to ensure highly efficient denitrification and phosphorus removal, it is preferable to control the aeration so as to adjust the concentration of dissolved oxygen in the mixed liquor to a predetermined value, whereby the anoxic condition for the denitrification and the anaerobic condition for releasing phosphorus from the sludge can be surely obtained in the succeeding agitating step.

The above and further objects and novel features of the invention will be more fully apparent from the detailed description when the same is read in connection with the accompanying drawings. It is to be understood, however, that the drawings are not intended as a definition of the limits of the invention.

BRIEF DESCRIPTION OF THE DRAWINGS

Referring to FIG. 4, a plant for conducting the activated sludge process according to the invention is designated by the reference numeral 30 and comprises a single tank 32 having a baffle plate 34 provided therein. The baffle plate 34 divides the interior of the tank 32 into two basins, that is, a basin 36 for introducing waste water into the tank 32 and a basin 38 for treating the waste water by the activated sludge contained in the tank 32. In the basin 36, the introduced waste water is pretreated by a small amount of the sludge contained therein. The plant 30 also comprises an agitating and aerating device 40 a part of which is immersed in the waste water sludge or mixed liquor held in the treatment basin 38. The device 40 includes a pair of pipes 42 and 44 which are connected to headers 41 and 43 disposed at the bottom of the treatment basin 38. As shown in FIG. 4, the header 41 of the pipe 42 is smaller than the header 43 of the pipe 44 and is housed therewithin. The headers have nozzles and the nozzles are aligned with each other. The pipe 42 is used to agitate the mixed liquor by ejecting a part of the mixed liquor from the nozzle of the header 41. In this case, a part of the mixed liquor is fed to the pipe 42 by, for example, a pump (not shown) which is provided in the treatment basin 38. On the other hand, the pipe 44 is used to aerate the mixed liquor. The air is fed by the pipe 44, mixed with the liquid from the nozzle of header 41, and the mixture of liquid and air is ejected from the nozzle of the header. That is, the mixed liquor is aerated by simultaneously ejecting a part of the mixed liquor and air from the nozzles of the headers 41 and 43. The air is fed to the pipe 44 by, for example, a blower 46.

Figure 5:
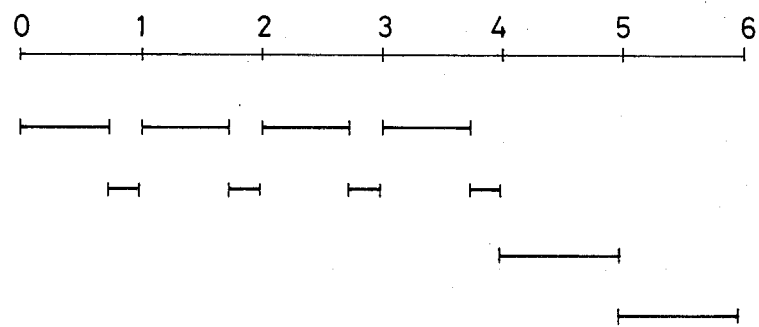
FIG. 5 is a time schedule along which the process of FIG. 4 is conducted.

In the process according to the invention, the waste water is continuously and gradually fed into the treatment basin 38 through the introduction basin 36. During the feeding of the waste water, it is treated by the activated sludge contained in the tank 32 in accordance with a time schedule an example of which is shown in FIG. 5. That is, the mixed liquor held in the treatment basin 38 is agitated by ejecting a part of the mixed liquor from the nozzle of the header 41. This agitating step is performed over a period of forty-five minutes. In this agitating step, the mixed liquor presents an anoxic condition and a succeeding anaerobic condition. In the anoxic condition, nitrate nitrogen included in the mixed liquor is subjected to reduction and organic material included therein is subjected to oxidization thereby causing denitrification. In the succeeding anaerobic condition, the aerobic bacteria included in the mixed liquor release phosphorus into the waste water in order to stay alive. Then, the mixed liquor is aerated by simultaneously ejecting a part of the mixed liquor and air from the nozzles of the headers 41 and 43. This aerating step is performed over a period of fifteen minutes. In this aerating step, ammonia nitrogen included in the mixed liquor is nitrified and changed into nitrate nitrogen while the bacteria excessively ingest phosphorus from the mixed liquor. As apparent from FIG. 5, a cycle consisting of the agitating and aerating steps is repeated four times. Thereafter, the settling step occurs for separating the agitated and aerated mixed liquor into a supernatant liquid. And then sludge and the supernatant liquid is then discharged as an effluent. The settling and discharging steps are each carried out over a period of one hour.

In the process mentioned above, it is preferable to control the feeding rate of air during the aerating step so that the anoxic condition and the succeeding anaerobic condition can be surely obtained in the agitating step. To this end, the plant 30 is provided with a DO meter 48 for measuring the concentration of dissolved oxygen in the mixed liquor. The DO meter includes a DO sensor 50 immersed in the mixed liquor and is associated with a computer 52 which controls the blower 46 on the basis of the measured concentration of dissolved oxygen so that this concentration is adjusted to a predetermined value. In the process which is conducted along the time schedule of FIG. 5, the concentration of dissolved oxygen is maintained at about 2 mg/l. The concentration maintained of course varies with the length of the agitating step and the organic material content of the waste water. In short, the concentration of dissolved oxygen should be maintained during the aerating step so that the anoxic condition and the anaerobic condition are surely obtained in the agitating step. In order to maintain the concentration of dissolved oxygen at the predetermined value, the feeding rate of air may be controlled by adjusting the speed of the blower 46 and/or by intermittently running the blower 46.

In the discharging step, the supernatant liquid is discharged through a decanter 54 which includes a conduit 56 pivotally mounted in the treatment basin 38, an overflow pipe 58 perpendicularly extending from the conduit 56 and having an overflow port 60 formed at its free end, and a pair of floats 62 pivotally connected to the free end of the overflow pipe 58 by a rod member 64. The decanter 54 can be pivoted about the longitudinal axis of the conduit 56 to follow the level of the supernatant liquid so that the supernatant liquid flows into the overflow pipe 58 through the overflow port 60 and is discharged out of the treatment basin 38 through the conduit 56. On the other hand, the settled sludge is reused for the treatment of new waste water introduced into the treatment basin 38, although a part of the settled sludge can be drawn out from the treatment basin 38 through a drain cock 66, if necessary.

During the settling and discharging steps, the feeding of waste water into the treatment basin 38 is stopped if the capacity of the tank 32 is small. In this case, it is expedient to use two tanks into which the waste water is alternately fed so that it is continuously treated. If the tank 32 has a large capacity, the feeding of the waste water into the treatment basin 32 may be continued during the settling and discharging steps. In this case, the fed waste water is subjected to a pre-treatment by the sludge so that the succeeding treatment can be effectively carried out.

When the waste water is treated by the process mentioned above, percentages of denitrification and phosphorus removal were above ninety percent. The following table showns a comparison between the process according to the invention and the prior process shown in FIGS. 1 and 2 with respect to the percentages of the denitrification and phosphorus removal:

activated sludge is contained so that a mixed liquor is formed of the waste water and the sludge in the treatment basin 68. In this case, it is necessary to pass the mixed liquor into the treatment basin 68 as a plug-flow so that the waste water is uniformly treated. The waste water is treated by the sludge in accordance with a time schedule such as that shown in FIG. 7. More specifically, a cycle consisting of an agitating step (hatched area in FIG. 7) and an aerating step (blank area in FIG. 7) is continuously repeated in the treatment basin 68 so that the waste water is treated for denitrification and phosphorus removal. The agitating step is performed over a period of forty-five minutes so that the mixed liquor presents an anoxic condition and a succeeding anaerobic condition. In the same way as in the process described above, denitrification is caused in the anoxic condition and the aerobic bacteria included in the sludge release phosphorus under the anaerobic condition in the mixed liquor for life preservation. Also, the aerating step is conducted over a period of fifteen minutes so that ammonia nitrogen included in the mixed liquor is nitrated and changed into nitrate nitrogen while the bacteria which have released phosphorus excessively ingest phosphorus from the mixed liquor. After the waste water is treated, it is continuously transferred to a settlement basin 70 and is separated into a supernatant liquid and the sludge. The supernatant liquid is discharged as an effluent from the settlement basin 70 and the settled sludge is returned to the treatment basin 68 for the treatment of waste water. In addition, a part of the settled sludge is drawn out from the settlement basin 70, if necessary.

Figure 1:
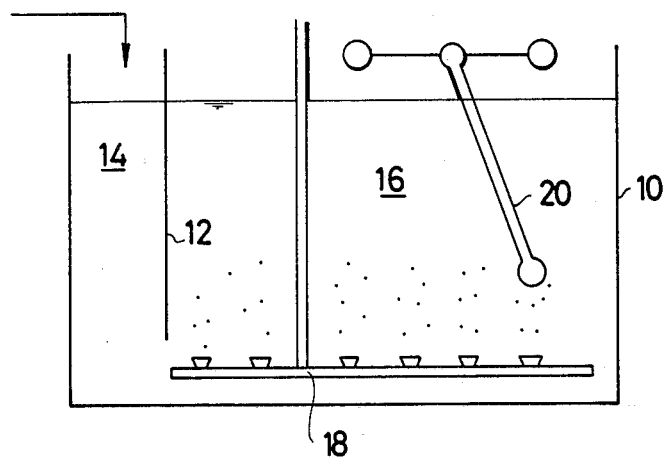
FIG. 1 is a diagrammatic view showing a conventional plant for conducting an activated sludge process for denitrification and phosphorus removal.
Figure 2:
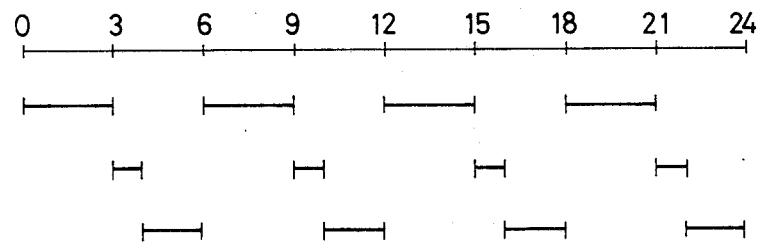
FIG. 2 is a time schedule along which the process of FIG. 1 is performed.
Figure 3:
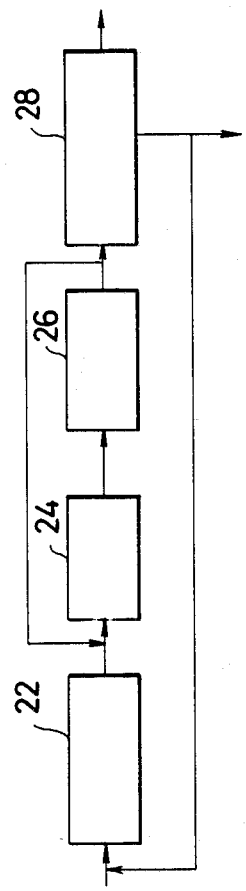
FIG. 3 is a flow chart of a conventional plant for conducting an activated sludge process wherein the waste water is continuously treated for denitrification and phosphorus removal.
Figure 4:
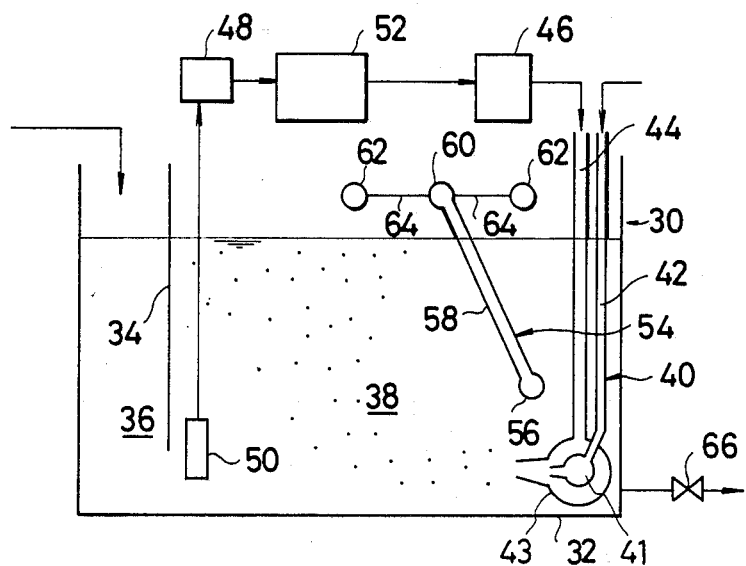
FIG. 4 is a diagrammatic view showing a plant for conducting an activated sludge process according to the invention.

In this process, the agitating and aerating steps may be conducted by the device 40 shown in FIG. 4 or by an agitator with impellers and an air diffuser as shown in FIG. 1. Also, it should be understood that the feeding rate of air may be controlled during the aerating step for the same reasons as in the process mentioned hereinbefore.

It is also possible to remove nitrogen and phosphorus from the waste water with a high efficiency (above 90%) by the second process.

In order to achieve the high efficiency phosphorus removal by the first and second processes according to the invention, it is necessary to suitably select the ratio of the agitating time to the aerating time as well as the time for completion of the cycle consisting of the agitating step and the aerating step.

Figure 8:
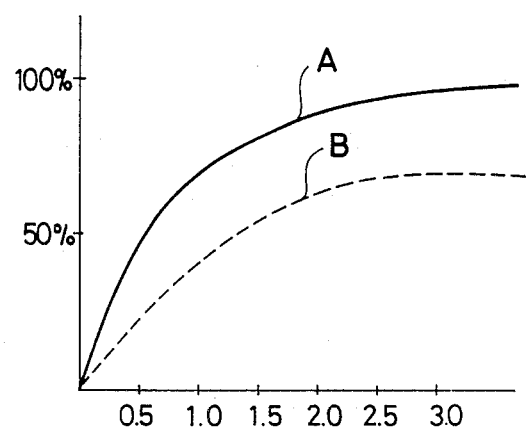
FIG. 8 is a graph showing the relationship between the percentage of phosphate removal and the ratio of the agitating time to the aerating time.

FIG. 8 is a graph showing how the percentage of phosphorus removal changes relative to the ratio of the agitating time to the aerating time. In FIG. 8, curve A represents the relationship when the cycle consisting of the agitating step and the aerating step is finished in one

TABLE

| | Prior Process | | | The Invention | | |
|---|---|---|---|---|---|---|
| | waste water | supernatant liquid | removal % | waste water | supernatant liquid | removal % |
| pH | 7.5 | 7.4 | — | 7.6 | 7.2 | — |
| BOD | 129 | 8.6 | 93.3 | 192 | 14.1 | 92.7 |
| T-N | 24.9 | 11.1 | 55.4 | 42.5 | 3.29 | 92.3 |
| T-P | 3.67 | 1.29 | 64.9 | 5.30 | 0.44 | 91.7 |

BOD: biochemical oxygen demand
T-N: total nitrogen
T-P: total phosphorus

Figure 6:
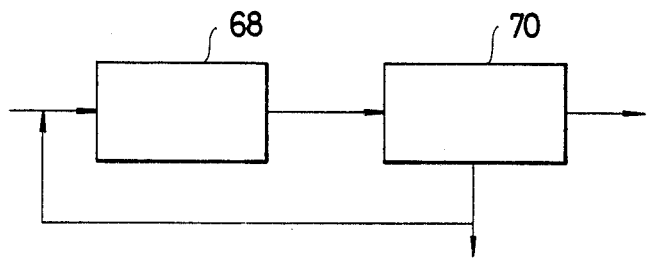
FIG. 6 is a flow chart for the activated sludge process according to the invention, wherein the waste water is continuously treated.
Figure 7:
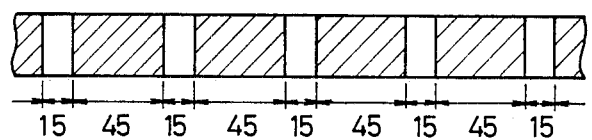
FIG. 7 is a time schedule along which the process of FIG. 6 is conducted.

FIGS. 6 and 7 show an activated sludge process of the invention for continuously treating waste water. As shown in FIG. 6, the waste water is continuously and gradually fed into a treatment basin 68 in which the hour and the curve B represents the relationship when the cycle is finished in four hours.

Figure 9:
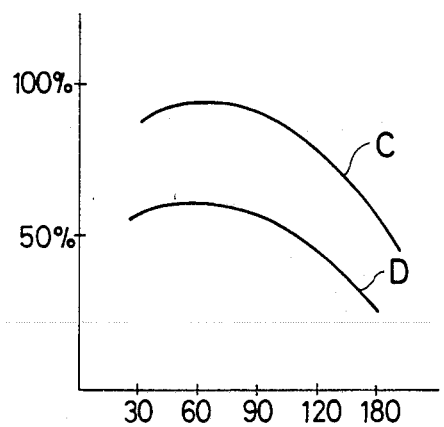
FIG. 9 is a graph showing the relationship between the percentage of phosphorus removal and the length of a cycle consisting of an agitating step and an aerating step.

FIG. 9 is a graph showing the relationship between phosphorus removal and the length of the cycle consisting of the agitating step and the aerating step. In FIG. 9, the curve C represents the relationship when the ratio of the agitating time to the aerating time is 3:1 and the curve D represents the relationship when the ratio is 1:1.

As is apparent from FIGS. 8 and 9, in order to achieve highly efficient phosphorus removal, the cycle consisting of the agitating step and the aerating step should be finished within two hours and the ratio of the agitating time to the aerating time should be between one to one and five to one.

It is apparent that the activated sludge method according to the invention can be performed using a relatively small plant.

According to the activated sludge method of the invention, it is possible to achieve highly efficient denitrification and phosphorus removal using a relatively small plant because the method does not require an anaerobic basin, corresponding to that of the abovementioned "Water SA", for eluting phosphorus from the aerobic bacteria. In other words, highly efficient denitrification and phosphorus removal can be obtained by merely using a single tank or two tanks.

While there has been described what is at present considered to be a preferred embodiment of the invention, it will be understood that various modifications may be made therein, and it is intended to cover in the appended claims all such modifications as fall within the true spirit and scope of the invention.

What we claim:

1. A method of removing nitrogen and phosphorus from waste water by using activated sludge including aerobic bacteria and changing alternately operational modes in a treatment basin, in accordance with a time schedule, which comprises the steps of:

adding the waste water continuously and gradually into a mixed liquor in a treatment basin which consists of the waste water and the sludge;

agitating the mixed liquor in said treatment basin during continuous and gradual adding of the waste water until it presents an anoxic condition and a succeeding anaerobic condition so that denitrification is caused in the anoxic condition and phosphorus is then released from the sludge in the anaerobic condition;

aerating the mixed liquor in the aerobic condition during the continuous and gradual adding of the waste water into the mixed liquor in the aerobic condition so that nitrification is accomplished while phosphorus is ingested by the sludge;

repeating a cycle consisting of said agitating and aerating steps at least two times so that each cycle is finished within two hours, the ratio of the agitating time to the aerating time being between one to one and five to one;

settling the agitated and aerated mixed liquor for separating it into a supernatant liquid and the sludge; and discharging the supernatant liquid as an effluent and reusing the settled sludge for the treatment of waste water.

2. The method as set forth in claim 1, wherein said settling step is conducted in said treatment basin while the feeding of the waste water thereinto is stopped, and a part of the settled sludge is drawn out from said treatment basin, if necessary.

3. The method as set forth in claim 2, wherein during said aerating step, the feeding rate of air is controlled so as to adjust the concentration of dissolved oxygen in the mixed liquor to a predetermined value for ensuring denitrification and phosphorus removal.

4. The method as set forth in claim 1, wherein said settling step is performed in said treatment basin while the feeding of the waste water thereinto is continued, and a part of the settled sludge is drawn out from said treatment basin, if necessary.

5. The method as set forth in claim 4, wherein during said aerating step, the feeding rate of air is controlled so as to adjust the concentration of dissolved oxygen in the mixed liquor to a predetermined value for ensuring denitrification and phosphorus removal.

6. The method as set forth in claim 1, wherein during said aerating step, the feeding rate of air is controlled so as to adjust the concentration of dissolved oxygen in the mixed liquor to a predetermined value for ensuring denitrification and phosphorus removal.

7. The method as set forth in claim 1, wherein said agitated and aerated mixed liquor is transferred to a settling basin and said settling step is performed therein, whereby the waste water is continuously treated, the settled sludge being returned to said treatment basin for the treatment of waste water.

8. The method as set forth in claim 7, wherein during said aerating step, the feeding rate of air is controlled so as to adjust the concentration of dissolved oxygen in the mixed liquor to a predetermined value for ensuring denitrification and phosphorus removal.

* * * * *